United States Patent
Crevecoeur et al.

(10) Patent No.: US 10,353,044 B2
(45) Date of Patent: Jul. 16, 2019

(54) METHODS AND SYSTEMS FOR DETERMINING A PARTICLE DISTRIBUTION

(71) Applicant: PEPRIC NV, Leuven (BE)

(72) Inventors: Guillaume Crevecoeur, Ledeberg (BE); Annelies Coene, Varsenare (BE); Luc Dupre, Sijsele (BE); Peter Vaes, Bonheiden (BE)

(73) Assignee: PEPRIC NV, Leuven (BE)

(*) Notice: Subject to any disclaimer, the term of this patent is extended or adjusted under 35 U.S.C. 154(b) by 1084 days.

(21) Appl. No.: 14/669,613

(22) Filed: Mar. 26, 2015

(65) Prior Publication Data

US 2015/0198689 A1    Jul. 16, 2015

Related U.S. Application Data

(63) Continuation-in-part of application No. PCT/EP2013/070136, filed on Sep. 26, 2013.

(30) Foreign Application Priority Data

Sep. 26, 2012 (GB) .................................. 1217228.4

(51) Int. Cl.
*G01R 33/60* (2006.01)
*G01R 33/385* (2006.01)
*G01N 24/10* (2006.01)

(52) U.S. Cl.
CPC ............. *G01R 33/60* (2013.01); *G01N 24/10* (2013.01); *G01R 33/385* (2013.01)

(58) Field of Classification Search
CPC .... G01R 33/60; G01R 33/441; G01R 33/345; G01N 24/10; G01N 24/08; G01N 24/084

(Continued)

(56) References Cited

U.S. PATENT DOCUMENTS 6,083,988 A * 7/2000 Becker .................. C07C 291/02
                                                    514/1.5
2007/0014727 A1* 1/2007 Rohrer .................... A61B 5/415
                                                    424/9.3

(Continued)

FOREIGN PATENT DOCUMENTS

GB       2221040 A      1/1990
GB       2489403 A     10/2012

(Continued)

OTHER PUBLICATIONS

Hirata, Hiroshi, et al. "Decoupling of automatic control systems in a continuous-wave electron paramagnetic resonance spectrometer for biomedical applications." NMR in Biomedicine 17.5 (2004): 295-302. APA.*

(Continued)

*Primary Examiner* — Christopher P McAndrew
(74) *Attorney, Agent, or Firm* — Workman Nydegger

(57) ABSTRACT

A system for determining a reconstruction of a particle distribution in an object based on electron paramagnetic resonance (EPR) measurement data of the object comprising the distribution of particles is described. The system comprises a data input for obtaining electron paramagnetic resonance measurement data of the object under study. The system also comprises a processor for processing the obtained data by applying a numerical model for solving a numerical inverse problem of deriving from the electron paramagnetic resonance measurement data a reconstruction of the particle distribution. The system furthermore comprises an output port for outputting data based on the derived reconstruction of the particle distribution.

16 Claims, 13 Drawing Sheets

(58) Field of Classification Search
USPC .......................................................... 324/316
See application file for complete search history.

(56) References Cited

U.S. PATENT DOCUMENTS

| | | | |
|---|---|---|---|
| 2011/0101956 A1* | 5/2011 | Thorn | G01D 4/004 324/76.11 |
| 2011/0148414 A1* | 6/2011 | Teughels | B82Y 15/00 324/316 |
| 2012/0072389 A1* | 3/2012 | Aldridge | G06N 5/04 706/54 |
| 2012/0223840 A1* | 9/2012 | Guymon | H04B 3/54 340/870.02 |
| 2014/0009159 A1 | 1/2014 | Vaes et al. | |

FOREIGN PATENT DOCUMENTS

| | | | | |
|---|---|---|---|---|
| SU | 1476362 A1 | 4/1989 | | |
| WO | 2010037800 A1 | 4/2010 | | |
| WO | 2010037801 A1 | 4/2010 | | |
| WO | WO 2010037800 A1 * | 4/2010 | ............. | B82Y 15/00 |
| WO | WO-2010037800 A1 * | 4/2010 | ............. | B82Y 15/00 |
| WO | 2012126968 A1 | 9/2012 | | |

OTHER PUBLICATIONS

Coffman, R. E. "Inhomogeneously broadened line shapes and information content of calculated paramagnetic resonance spectra of biological molecules containing high-spin iron (III)." The Journal of Physical Chemistry 79.11 (1975): 1129-1136.*

Hirata, Hiroshi, et al. "Decoupling of automatic control systems in a continuous-wave electron paramagnetic resonance spectrometer for biomedical applications." NMR in Biomedicine 17.5 (2004): 295-302. (Year: 2004).*

Coffman, R. E. "Inhomogeneously broadened line shapes and information content of calculated paramagnetic resonance spectra of biological molecules containing high-spin iron (III)." The Journal of Physical Chemistry 79.11 (1975): 1129-1136. (Year: 1975).*

Coene et al., "Quantitative Estimation of Magnetic Nanoparticle Distributions in one Dimension Using Low-Frequency Continuous Wave Electron Paramagnetic Resonance," J. Phys. D: Appl. Phys., Jun. 19, 2013, pp. 1-10, vol. 46, No. 24.

Deng et al., "Progressive EPR Imaging with Adaptive Projection Acquisition," Journal of Magnetic Resonance, Jun. 1, 2005, pp. 177-187, vol. 174, No. 2.

Flynn et al., "A Biomagnetic System for In Vivo Cancer Imaging," Phys. Med. Biol., Mar. 21, 2005, pp. 1273-1293.

Gamarra et al., "Ferromagnetic Resonance for the Quantification of Superparamagnetic Iron Oxide Nanoparticles in Biological Materials," International Journal of Nanomedicine, 2010, pp. 203-211, vol. 5.

Gleich et al.,"Tornographic Imaging Using the Nonlinear Response of Magnetic Particles", Nature, Jun. 30, 2005, pp. 1214-1217, vol. 435.

Great Britain Search Report for corresponding Great Britain Application No. 1217228.4, dated Dec. 4, 2012.

International Search Report for corresponding International PCT Application No. PCT/EP2013/070136, dated Feb. 13, 2014.

Jingchuan et al., "A Simplified Apparatus for EPR Imaging," Meas. Sci. Technol., Jun. 1, 1996, pp. 904-907, vol. 7, No. 6.

Tsai et al., "Magnetic Resonance Multi-view Inverse Imaging (MV Inl) for Human Brain," ISMRM-ESMRMB Joint Annual Meeting Proceedings, May 1, 2010, p. 4898.

* cited by examiner

METHODS AND SYSTEMS FOR DETERMINING A PARTICLE DISTRIBUTION

FIELD OF THE INVENTION

The invention relates to the field of electron paramagnetic resonance. More specifically the present invention relates to methods and systems for reconstructing particle distribution data in an object based on electron paramagnetic resonance measurement data and computer related aspects based thereon, as well as to an electron paramagnetic resonance system comprising such a reconstruction system.

BACKGROUND OF THE INVENTION

Magnetic nanoparticles are increasingly applied for diagnostic and therapeutic purposes. They show a set of interesting physical properties including controllable sizes ranging from ten to several hundred nanometers, a high saturation magnetization and superparamagnetic behaviour. Their small size enables them to penetrate the endothelial walls that form the interface between circulating blood or lymph and the rest of the vessel wall and even to cross cell membranes. By custom functionalisation of the particles' surfaces, they can selectively bind to a defined biological entity (like cells or degraded extracellular matrix molecules) and deliver drugs or therapeutic DNA for targeted therapy.

By applying a controlled external magnetic field it is possible to perform different actions on the magnetic particles such as applying a mechanic force on the nanoparticles to guide them to a specific location and retaining them there for drug release (magnetic drug targeting, magnetic gene transfection); specifically heating the magnetic nanoparticles (magnetic hyperthermia); changing the local magnetic field in the particle's environment (MRI contrast agents, magnetic cell labelling); generating a specific magnetic signal that can be read from the outside (magnetic nanoparticle imaging); etc. All applications will benefit from a quantitative knowledge of the magnetic nanoparticle distribution to increase suitability, patient safety and efficacy.

A non-invasive quantitative technique for magnetic nanoparticle imaging is at present not established, although several proposals have been made in literature. A first suggestion is Magnetic Particle Imaging (MPI) which is able to image the magnetic particles at very high speed, but is unable to quantitatively determine the concentration of the magnetic nanoparticles. The technique was suggested by Gleich and Weizenecker in Nature 435 (2005) pp 1214-1217. The principle of MPI is based on the nonlinearity of the particles' magnetization curve. When subject to an oscillating magnetic field, the spectrum of the responding magnetization contains not only the base frequency but also higher harmonics that are exploited for imaging.

An alternative is to use magnetorelaxometry measurements as proposed by Flynn and Bryant in Physics in Medicine and Biology 50 (2005) 1273-1293. Magnetic nanoparticles can be activated using an external magnetic field where the single domains of the superparamagnetic nanoparticles are aligned with the local magnetic field. When switching off the external magnetic field, magnetic relaxation occurs following two different relaxation processes (Brown and Néel). The magnetic field originating from the particles in the different positions can be measured using sensitive magnetic field sensors such as superconducting quantum interference devices (SQUIDS).

Electron paramagnetic resonance (EPR) and pulsed EPR detection as described by Teughels and Vaes in International patent application WO2010/037800 developed by Teughels and Vaes is able to sense the concentration of particles. Quantification of the concentration in a single voxel has been reported by Gamarra in International journal of Nanomedicine 5 (2010) pp 203-211. There is still room for an accurate spatial reconstruction of magnetic nanoparticles starting from EPR measurements.

SUMMARY OF THE INVENTION

It is an object of embodiments of the present invention to provide efficient methods and systems for spatially reconstructing magnetic nanoparticles using Electron Paramagnetic Resonance (EPR) effect measurements.

It is an advantage of embodiments according to the present invention that methods and systems are provided that allow determining the values of concentration of magnetic nanoparticles in different points in space starting from measurements in a single point in space.

It is an advantage of embodiment according to the present invention that systems and methods are provided that are based on solving an inverse problem whereby a model interprets in a correct way the concentration distribution, resulting in more accurate particle distribution data obtained.

The object is obtained by systems and methods according to embodiments of the present invention.

The present invention relates to a system for determining a reconstruction of a particle distribution in an object based on electron paramagnetic resonance (EPR) measurement data of the object comprising the distribution of particles, the system comprising a data input for obtaining electron paramagnetic resonance measurement data of the object under study, a processor for processing the obtained data by applying a numerical model for solving a numerical inverse problem of deriving from the electron paramagnetic resonance measurement data a reconstruction of the particle distribution, an output port for outputting data based on the derived reconstruction of the particle distribution. It is an advantage of embodiments according to the present invention that an accurate determination of the distribution of the particles in an object can be determined, i.e. that an accurate quantitative image of the particles in an object can be obtained in the sense that the shape of the distribution as well as the values of the concentrations in the various points in space can be obtained.

The processor may be adapted for deriving a reconstruction of the particle concentration profile. It is an advantage of embodiments according to the present invention that not only the distribution but also a concentration profile of particles in an object, expressing the amount of particles at a given position, can be accurately obtained.

The processor may comprise a quality determinator for determining a measure of the quality of the reconstructed particle distribution. It is an advantage of embodiments according to the present invention that the quality of the reconstructed particle distribution can be determined and outputted. The latter allows e.g. a more accurate interpretation of the obtained results.

The system furthermore may comprise a controller for controlling the processing of the obtained data, as function of a determined measure of quality of the reconstructed particle distribution. It is an advantage of embodiments according to the present invention that the quality of the reconstructed particle distribution can be fine-tuned to obtain a predetermined quality so that a minimum quality requirement can be obtained.

The controller may comprise a parameter selection means for selecting a parameter of the numerical model. It is an advantage of embodiments according to the present invention that fine-tuning can include adjusting the numerical modeling, thus allowing an internal optimization loop for determining the best reconstruction.

The parameter selection means may be adapted for altering a set of eigenvalues of the numerical problem solved using the numerical model, depending on the determined measure of quality of the reconstructed particle distribution. It is an advantage of embodiments according to the present invention that an automated and/or automatic optimization of the numerical model can be performed by the processing unit, thus allowing to derive the reconstructed particle distribution in a good, improved or even optimum way.

The system may comprise a feedback loop comprising the quality determinator and wherein the feedback loop is adapted for controlling the system so as to obtain further electron paramagnetic resonance measurement data of the object. Altering of the electron paramagnetic resonance measurement data can comprise requesting alternative input data or can be performed in an automated and/or automatic way.

The data input may comprise an EPR measurement system for measuring EPR measurement data, wherein the feedback loop is adapted for controlling the EPR measurement system for obtaining further measurement data with an altered measurement condition for the object. It is an advantage of embodiments of the present invention that systems allow to implement, e.g. in an automated and/or automatic way although not restricted thereto, improved measurement conditions allowing to obtain an improved reconstruction of the particle distribution.

The feedback loop may be adapted for controlling the data input so as to obtain further EPR measurement data. It is an advantage of embodiments of the present invention that systems are provided that allow, adjusting the required measurement input, when the predetermined, e.g. desired, reconstruction quality is not obtained.

The feedback loop may be adapted for controlling the data input so as to obtain further EPR measurement data of the object sampled at different or additional relative positions of a magnetic field of the EPR system with respect to the object, sampled using different or additional gradient magnetic fields applied to the object, or sampled using a different spatial sampling point distribution over the sample. Different parameters determining the EPR measurement data collection can be tuned for obtaining optimal reconstruction quality.

The present invention also relates to a system for obtaining electron paramagnetic resonance data of an object, the system comprising a system for determining a reconstruction of a particle distribution in an object as described above.

The present invention relates to a method for determining a reconstruction of a particle distribution in an object based on electron paramagnetic resonance (EPR) measurement data of the object comprising the distribution of particles, the method comprising obtaining electron paramagnetic resonance measurement data of the object under study, processing the obtained data by applying a numerical model for solving a numerical inverse problem of deriving from the electron paramagnetic resonance measurement data a reconstruction of the particle distribution, and outputting data based on the derived reconstruction of the particle distribution.

Said processing may comprise deriving a reconstruction of the particle concentration profile.

The processing may comprise determining a measure of the quality of the reconstructed particle distribution.

The method may comprise controlling the processing of the obtained data, as function of the determined measure of quality of the reconstructed particle distribution.

Said controlling may comprise selecting a parameter of the numerical model.

Selecting may comprise altering a set of eigenvalues of the numerical problem solved using the numerical model, depending on the determined measure of quality of the reconstructed particle distribution.

The method may comprise obtaining further electron paramagnetic resonance measurement data of the object, based on the determined measure of quality of the reconstructed particle distribution.

The method may comprise obtaining further measurement data for an altered measurement condition for the object.

The method may comprise controlling the data input so as to obtain further EPR measurement data.

The method may comprise obtaining further EPR measurement data of the object sampled at different or additional relative positions of a magnetic field of the EPR system with respect to the object, sampled using different or additional gradient magnetic fields applied to the object, or sampled using a different spatial sampling point distribution over the sample.

The present invention also relates to an image or volumetric image obtained using a system as described above or using a method as described above.

The present invention also relates to a computer program product for, if implemented on a processing unit, performing the method as described above.

The present invention also relates to a data carrier comprising a computer program product as described above or the transmission thereof over a network.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
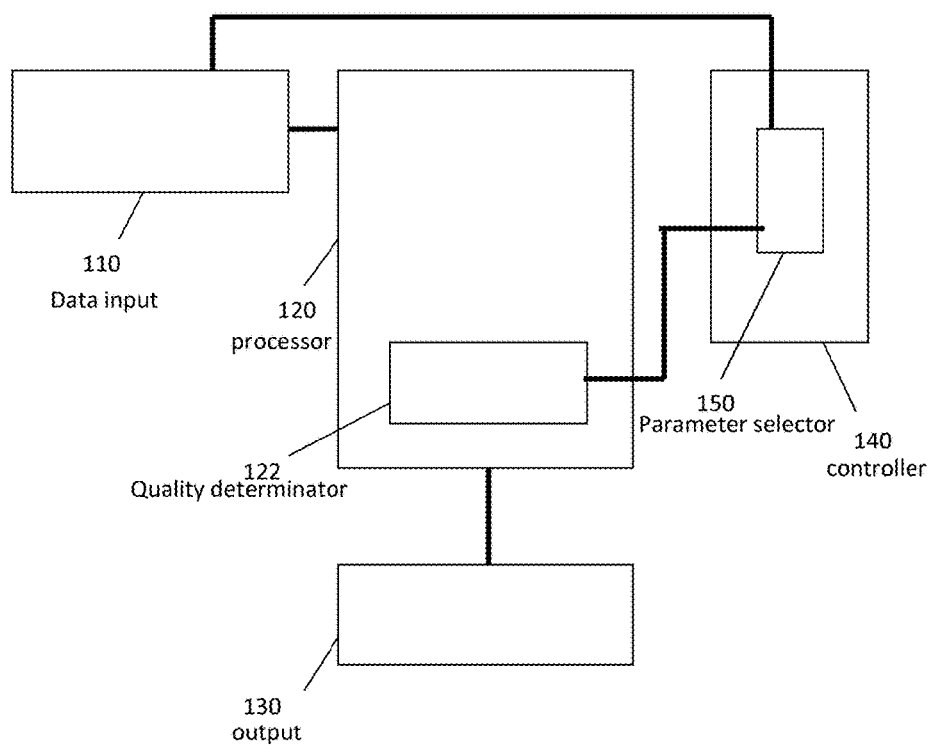
FIG. 1 shows a schematic representation of an exemplary system according to an embodiment of the present invention.
Figure 2:
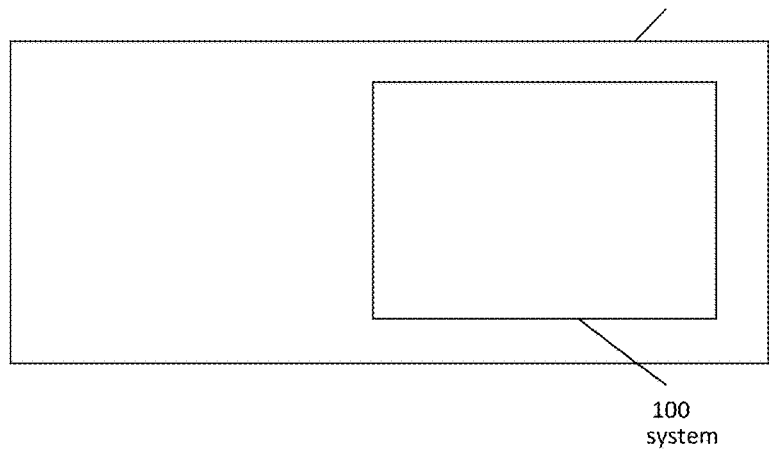
FIG. 2 illustrates an electron paramagnetic resonance measurement system comprising a distribution reconstruction means as described in FIG. 1.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In embodiments of the present invention, methods and system are provided for gathering information about an object under test that includes particles presenting paramagnetic properties. These particles may be introduced in any suitable way such as for example by administering, by mixing, by pouring, etc. More particularly, the information gathered is based on or related to the distribution of the particles representing paramagnetic properties in the object. Particles comprising paramagnetic properties may be nano-particles, typically referring to particles having a critical dimension, e.g. diameter, in the range of 1 nm to 1000 nm. The nano-particles or magnetic nano-particles may be single domain particles. The particles may be magnetic particles with a broad line width, reference may be made to a line width of 3 MHz or larger, e.g. in a range from 3 MHz to 400 MHz. Reference may be made to particles having a line width, e.g. a full width at half maximum FWHM, larger than 5%, e.g. larger than 10%, e.g. larger than 20% of the central line frequency. It is to be noticed that embodiments of the present invention can be advantageously applied to spin systems with a broad line width, although embodiments of the present invention are not limited thereto and can be applied to spin systems with any line width, i.e. including spin systems with narrow line width.

Where in embodiments according to the present invention reference is made to an object under study, such an object may be a non-living object or a living object. In some embodiments—the present invention not being limited thereto—the object may be a body of a living creature, such as for example an animal or human body. The object under study according to embodiments of the present invention are paramagnetic objects. Embodiments of the present invention can also be used for in-vitro testing, e.g. for the quantification of cells linked with the paramagnetic objects). Embodiments of the invention allow to reconstruct the distribution of the paramagnetic objects with a high sensitivity and accuracy. Examples of applications include 3D imaging. Objects under study may be paramagnetic objects as of nature or may be made at least partially paramagnetic by adding, e.g. through administering, paramagnetic particles, such as paramagnetic nanoparticles, to the object. The administering step may be performed prior to application of the method according to embodiments of the present invention for detecting electron paramagnetic resonance of the object under study.

In a first aspect, the present invention relates to a system for reconstructing or determining a reconstruction of a particle distribution in an object. Such determining is based on electron paramagnetic resonance (EPR) measurement data of the object comprising the distribution of particles. Embodiments according to the present invention can be used for all types of electron paramagnetic resonance (EPR) detection, such as for example for detecting paramagnetic particles with broad line width—embodiments of the present invention not being limited thereto. The system, also referred to as reconstruction system according to embodiments of the present invention comprises a data input for obtaining electron paramagnetic resonance measurement data of the object under study, a processor for processing the obtained data by applying a numerical model for solving a numerical inverse problem of deriving from the electron paramagnetic resonance measurement data a reconstruction of the particle distribution, and an output port for outputting data based on the derived reconstruction of the particle distribution. By way of illustration, embodiments of the present invention not being limited thereto, an exemplary system for reconstructing a particle distribution, e.g. a concentration profile, will be described with reference to FIG. 1 illustrating standard and optional features of such an embodiment. The reconstruction system 100 shown in FIG. 1 comprises a data input 110 for obtaining electron paramagnetic resonance measurement data. Such a data input may be an input port via which previously recorded electron paramagnetic resonance measurement data is received. Alternatively, such a data input may include an electron paramagnetic resonance system for recording the measurement data. The measurement data as such may be data recorded through any suitable measurement technique. One example are the measurement techniques as described in the international patent applications WO 2010/037800 and/or in international patent application WO 2010/037801, or in particular techniques as described e.g. in international patent application PCT/EP2012/055042 or in GB patent application GB1104758.6.

The system furthermore comprises a processor 120. As described above, such a processor typically may be adapted for processing the obtained data by applying a numerical model for solving a numerical inverse problem of deriving from the electron paramagnetic resonance measurement data a reconstruction of the particle distribution. One example of an implementation of such a numerical model will be described later. Nevertheless, embodiments are not limited thereto. In general the numerical modeling technique comprises input parameter values and output values. In the present examples, the input typically is the particle distribution, while the output of the system are the simulated signals in the sensors. The numerical inverse problem comprises using this numerical modeling so to determine the parameter values that correspond with the measured signals. According to one embodiment, the processor comprises a quality determinator 122, allowing to determine a measure of the quality of the reconstructed particle distribution. Quality may e.g. express the way the reconstruction coincides or approaches the measurements.

The system also comprises an output port for outputting information regarding the particle distribution, e.g. a concentration profile, of the particles in the object.

In some embodiments, the reconstruction system 100 also comprises a controller for controlling the processing of the obtained data as function of the determined measure of quality of the reconstruction. Such a controlling may be adapted for controlling the processor, e.g. by adjusting the numerical modeling. One way of adjusting the numerical modeling may be by selecting different numerical modeling parameters and the processor therefore may be equipped with a parameter selecting means. Selection of different numerical modeling parameters may be performed based on predetermined algorithms, a neural network, look up tables, according to predetermined rules, etc. One example of adjusting may be selecting the number or the specific set of eigenvalues used in the problem to be solved. For example, when the quality is insufficient, the number of eigenvalues used may be increased or decreased to deal therewith. Other examples of rules that can be implemented may make use of the condition where the difference between measured and simulated signals is smaller than a certain tolerance or if the difference between the particle distribution in a certain iteration compared to the previous one is smaller than a certain tolerance. The difference can in one example be expressed as a least-squares difference (L2-norm), another norm, correlation coefficients, etc.

In another embodiment, the system comprises a feedback loop, and controlling the system as function of the quality does not only affect the reconstruction process as such, but also the measurement data used. In other words, the control system may be adapted for controlling the system so as to obtain further electron paramagnetic resonance measurement data of the object. Such further electron paramagnetic resonance measurement data may for example comprise measurement data recorded with an altered measurement condition for the object. Such measurement data may be for example data sampled at different or additional relative positions of a magnetic field of the EPR system with respect to the object, sampled using different or additional gradient magnetic fields applied to the object, or sampled using a different spatial sampling point distribution over the sample.

According to one aspect of the present invention, the invention also relates to an EPR system comprising a reconstruction system as described above. The EPR system as such may for example be a system as described in any of the international patent applications WO 2010/037800 and/or in international patent application WO 2010/037801, or in particular techniques as described e.g. in international patent application PCT/EP2012/055042 or in GB patent application GB1104758.6.

Figure 3:
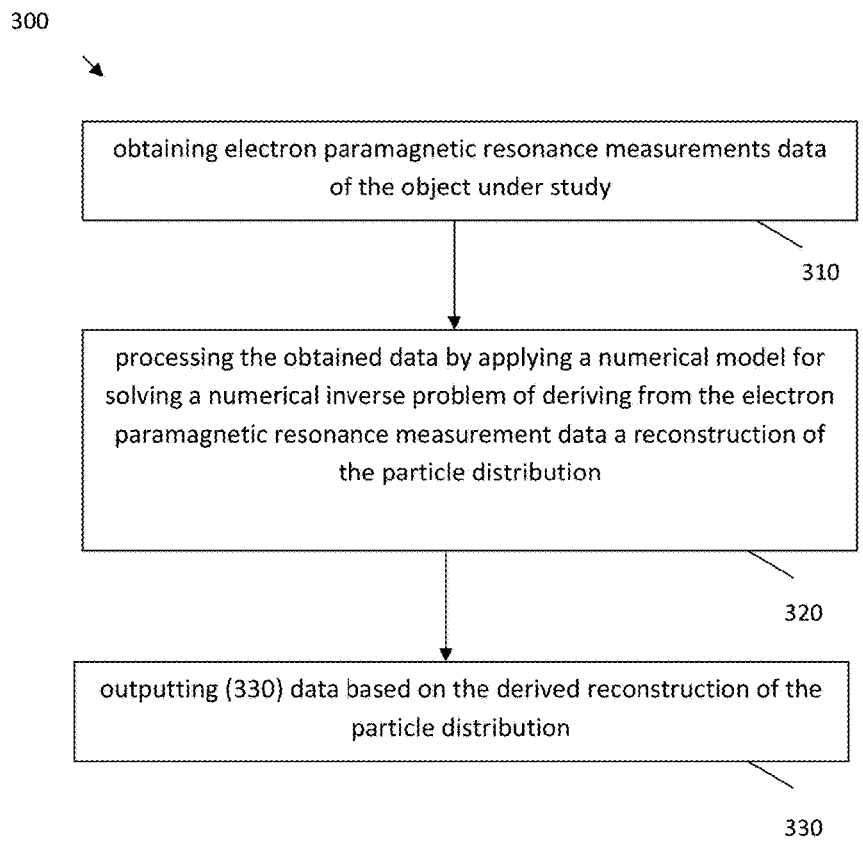
FIG. 3 illustrates a schematic overview of steps in an exemplary method for reconstructing a particle distribution in an object, according to an embodiment of the present invention.

In another aspect, embodiments of the present invention relate to a method for reconstructing or determining a reconstruction of a particle distribution in an object based on electron paramagnetic resonance (EPR) measurement data of the object. The reconstructed distribution may be or provide a concentration profile of the particles in the object. The particle distribution envisaged thereby is a distribution of particles comprising paramagnetic properties, as described above. Different steps of a method according to an embodiment of the present invention are further illustrated with reference to FIG. 3, embodiments of the present invention not being limited thereby. The method according to an embodiment comprises in a first step obtaining 310 electron paramagnetic resonance measurement data of the object under study. Such obtaining data may comprise merely receiving the data via an input port. Alternatively, obtaining the data may include performing the electron paramagnetic resonance measurements and receiving the data thereof in the reconstruction system. The method also comprises processing 320 the obtained data by applying a numerical model for solving a numerical inverse problem of deriving from the electron paramagnetic resonance measurement data a reconstruction of the particle distribution.

Figure 4:
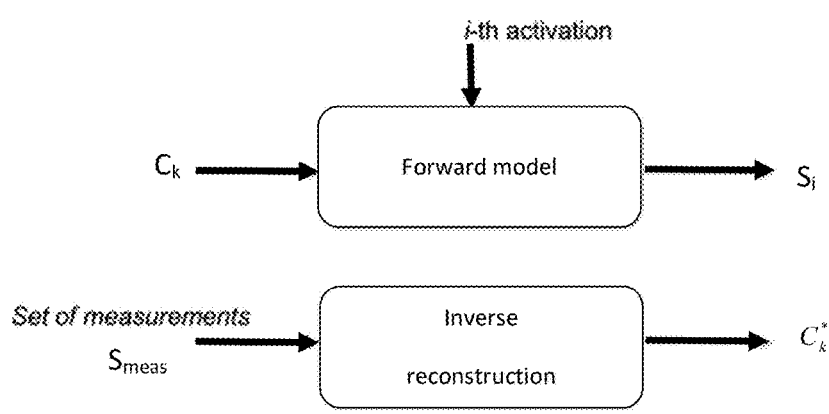
FIG. 4 illustrates an example of an inverse modeling step as can be applied in a method for reconstructing a particle distribution in an object according to an embodiment of the present invention.

A schematic overview of an example of how to apply a numerical model for solving a numerical inverse problem is illustrated in FIG. 4. Typically solving a numerical inverse problem comprises a step of applying an inverse reconstruction whereby based on the measurement data obtained a concentration is derived. A theoretical description of how such inverse model can be solved will be described later. Furthermore, besides performing the inverse reconstruction, typically also a so-called forward model is applied, whereby starting from a determined concentration, the estimated measurement results are derived. Such forward calculation, which needs to include information regarding the measurement conditions, can for the present case relate to deriving concentrations based on performed EPR measurements.

The method furthermore comprises outputting 330 data based on the derived reconstruction of the particle distribution. The method may be implemented such that it operates automated and/or automatic. It may be implemented in a processor and may be based on predetermined algorithms, using predetermined rules and/or look up tables, make use of a neural network for its processing, . . . .

It is an advantage of at least some embodiments of the present invention that the quality of the reconstruction can be monitored. In some embodiments, the quality (or a measure/metric expressing the quality) of the reconstruction is not only monitored, but it is also tuned to reach a predetermined value, so that an accurate interpretation of the results obtained can be envisaged. When the required or envisaged quality is not obtained by the reconstruction, different actions are possible.

In some embodiments, an internal feedback loop is installed and the quality can be improved or optimized by altering the processing of the obtained data. The latter may include using a certain numerical model, altering the numerical model used, e.g. by altering a set of eigenvalues of the numerical problem solved using the numerical model, etc.

In some embodiments, if the envisaged quality is not obtained, further electron paramagnetic resonance measurement data of the object are obtained or used. The method then may comprise obtaining further measurement data for an altered measurement condition for the object. Obtaining such further EPR measurement data thereby may for example comprise obtaining further EPR measurement data of the object sampled at different or additional relative positions of a magnetic field of the EPR system with respect to the object, sampled using different or additional gradient magnetic fields applied to the object, or sampled using a different spatial sampling point distribution over the sample.

Other features and optional steps may correspond with the functionality of components described with reference to systems for reconstructing particle distribution based on electron paramagnetic resonance measurements, as described.

In one aspect, embodiments of the present invention also relate to computer-implemented methods for performing at least part of the methods as described above or to corresponding computing program products. Such methods may be implemented in a computing system, such as for example a general purpose computer. The computing system may comprise an input means for receiving data. The system may be or comprise a data processor for processing data, e.g. the electron paramagnetic resonance data of the single domain particles. The computing system may include a processor, a memory system including for example ROM or RAM, an output system such as for example a CD-rom or DVD drive or means for outputting information over a network. Conventional computer components such as for example a keyboard, display, pointing device, input and output ports, etc also may be included. Data transport may be provided based on data busses. The memory of the computing system may comprise a set of instructions, which, when implemented on the computing system, result in implementation of part or all of the standard steps of the methods as set out above and optionally of the optional steps as set out above. Therefore, a computing system including instructions for implementing part or all of a method as described above is not part of the prior art.

Further aspect of embodiments of the present invention encompass computer program products embodied in a carrier medium carrying machine readable code for execution on a computing device, the computer program products as such as well as the data carrier such as dvd or cd-rom or memory device. Aspects of embodiments furthermore encompass the transmitting of a computer program product over a network, such as for example a local network or a wide area network, as well as the transmission signals corresponding therewith.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention.

As indicated, without wishing to be bounded by theory, the fact that the numerical inverse problem can be solved using a numerical model can be seen based on the theoretical considerations given below.

The gathering of information regarding the magnetic nanoparticles and its translation into a numerical problem typically includes the following:

(i) Measurement associated to single voxels with fixed concentration in different points in space. Such measurements can be performed by measuring a certain known amount of concentration in a certain volume in space, such volume being referred to as single voxel. Such a measurement is thus sensitive to the amount of concentration in that volume. Particular measurements are performed for fixed positions in space of the single voxel. The measurement may for example be performed by measurement of the resonance in measurement coils, whereby a static excitation coil is used. Resonance EPR measurements may be performed as known by the person skilled in the art.

(ii) Use of a 'system matrix' A that links the magnetic nanoparticles concentration in a certain point in space to the measurement. A is based on the measurements performed in step (i). An element (i,j) in the system matrix A corresponds with the sensitivity of the i-th measurement to the j-th position. The j-th position corresponds with a certain voxel having a certain amount of concentration. This element can also be seen as a gain factor where the concentration in the j-th position is multiplied with this gain factor resulting in the measurement. The i-th measurement may correspond with the i-th measurement position of the sample. The i-th measurement may also correspond with a different excitation of the internal state of the sample through the use of gradients.

(iii) It is possible to build the matrix A, e.g. by moving the sample or by exciting the internal state of the sample through the use of gradients. The element (i,j) can be determined by placing a certain known amount of concentration of magnetic nanoparticles in a voxel at the j-th position and measure for these magnetic nanoparticle in the i-th measurement position. Another possibility is to build A in such a way that the element (i,j) in matrix A corresponds with a concentration in a voxel at the j-th position but where the i-th measurement is done for a j-th spatial gradient of the excitation coils in the measurement apparatus. By considering distinct gradients and measure at the distinct measurement positions, we can determine the different elements in A.

(iv) Synthesis of concentrations in different points in space using vector C, and synthesis of different measurements in vector V. Typically, the following relationship can be derived:

$$V_m = AC$$

wherein $V_m$ denotes the modeled responses. An element in the vector C corresponds with the value of a concentration in a voxel at a certain position. These positions can be determined by discretizing the volume consisting of magnetic nanoparticles in different voxels. Each position of the voxel corresponds thus with an element in the vector C.

(v) Starting from the measured responses $V_{meas}$, the intention is then to reconstruct the real concentrations C* in space using the following relationship. An element in the vector Vmeas may correspond with the measurement at a certain position of the sample or with the measurement that corresponds with a certain applied gradient field. When varying the position of a sample consisting of magnetic nanoparticles in a single voxel, Vmeas corresponds with the measurement.

$$C^* = A^\dagger V_{meas}$$

(vi) The reconstruction (v) is possible by performing an inversion based on the singular value decomposition (SVD) of the matrix A: $A = USV^T$. The reconstructed concentrations in each voxel are given by $$C^* = \sum_{k=1}^{r} \frac{u_k^T V_{meas}}{s_k} v_k$$

with singular values $s_k$ (from matrix A) and $u_k$, $v_k$ the eigenvectors in the matrices U, V. As is illustrated in embodiments of the present invention the accuracy of the reconstruction can be further optimized by a good, improved or optimal choice of the parameter r in the above formula and a good, improved or optimal system matrix choice A. It is to be noted that there exist a number of different methods for obtaining C*.

In application of embodiments according to the present invention, gradient fields can be used for 'spatially encoding' the volume using a magnetic field $\vec{H}(\vec{r})$ that is spatially dependent ($\vec{r} = (x,y,z)$). Using the applied magnetic field $\vec{B}(\vec{r}) = \mu_0 \vec{H}(\vec{r})$, the volume under study has a magnetization $\vec{M}(\vec{r})$. In the most general way, the measured signal S can be expressed as (superposition):

$$S \approx \int_V F(\vec{B}(\vec{r}) \cdot \vec{n}, C(\vec{r})) dV \qquad (1)$$

where F is determined by the amplitude of the measured signal, taking into account the angular dependency of the measured signal (i.e. the measurement angle) and the concentration. The amplitude of the measured signal corresponds with 2*Effect(0°), being twice the electron paramagnetic resonance effect, as also known from U.S. patent application Ser. No. 14/006,153 incorporated herein by reference. The angular dependency is taken into account by performing a scalar multiplication between the measured signal and the normal axis, corresponding with the sensitive axis of the sensor. In the case of homogeneous activation and 1-voxel quantification, one has $$S \approx \int_V F(B_{hom}, C_{hom}) dV = V * F(B_{hom}, C_{hom}) \qquad (2)$$

with V the volume of the sample, $B_{hom}$, $C_{hom}$ defined for the single voxel. It is approximated that the function F will also hold when using multiple voxels. When discretizing the volume, (1) becomes:

$$S \approx \sum_{k=1}^{N} F(L_k, C_k) \Delta V_k \quad (3)$$

with $L_k$ the value of $\vec{B}(\vec{r}) \cdot \vec{n}$ within that voxel and $\Delta V_k$ the volume of each voxel (can be chosen the same for each voxel using regular grid). In at least some embodiments, the aim is to reconstruct $C_k$ by using fields, i.e. $L_k$ different from each other, and multiple measurements.

By using multiple activations (i=1, ..., $N_a$ with total activations $N_a$), it is possible to generate different $L_{i,k}$ because of the spatially (and directional) varying magnetic fields. Different possibilities exist to generate spatially varying magnetic fields.

A first possibility is to use a gradient coil configuration, i.e. instead of using Helmholtz coils, coils can be placed as Maxwell coils.

Each signal is then represented by $$S_i \approx \sum_{k=1}^{N} F(L_{i,k}, C_k) \Delta V_k \quad (i = 1, \ldots, N_a) \quad (4)$$

Starting from the $S_i$ measurements one aims to reconstruct $C_k$.

By way of illustration, embodiments of the present invention not being limited thereto, exemplary results are shown, illustrating features and advantages as can be used in embodiments or the present invention.

Figure 5:
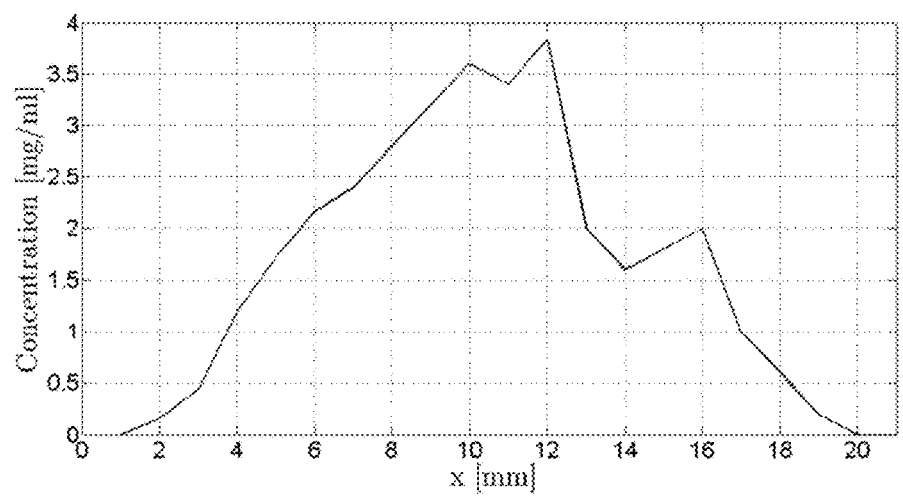
FIG. 5 illustrates assumed concentrations in a volume, as used in simulations illustrating features according to embodiments of the present invention.
Figure 5:
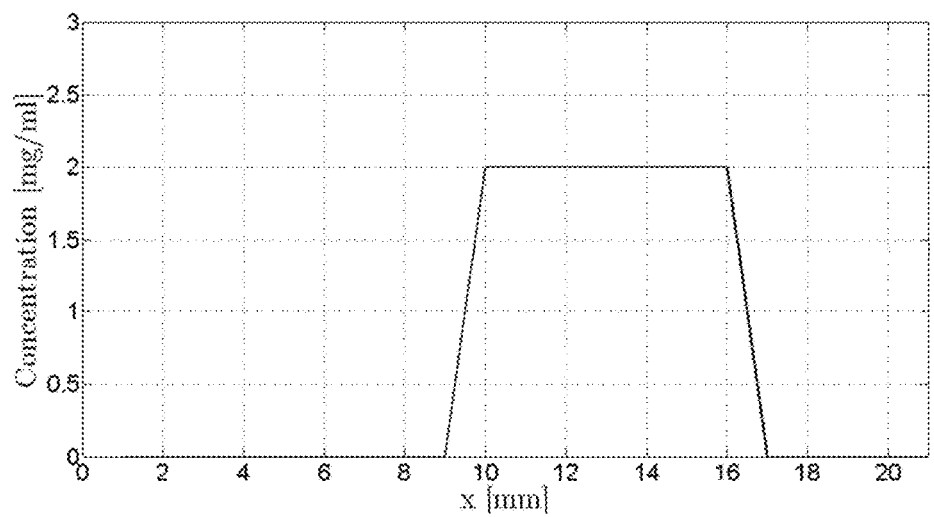

In a first example, illustrating numerical results, it is assumed that there is a certain test concentration that fluctuates 1D (x-direction). If there is for example a volume of 20.4×12×16.8 mm³, one wants to reconstruct the particles along the 20.4 side. FIG. 5 illustrates two test concentrations that were used in the simulations. The concentration thereby is defined here as the concentration in a volume 1×12×16.8 mm³.

In the present example, use is also made of the following calibration function $f(B,C)$, which is function of the applied magnetic induction B and the concentration C whereby use is made of interpolation for continuous B and C values.

Figure 7:
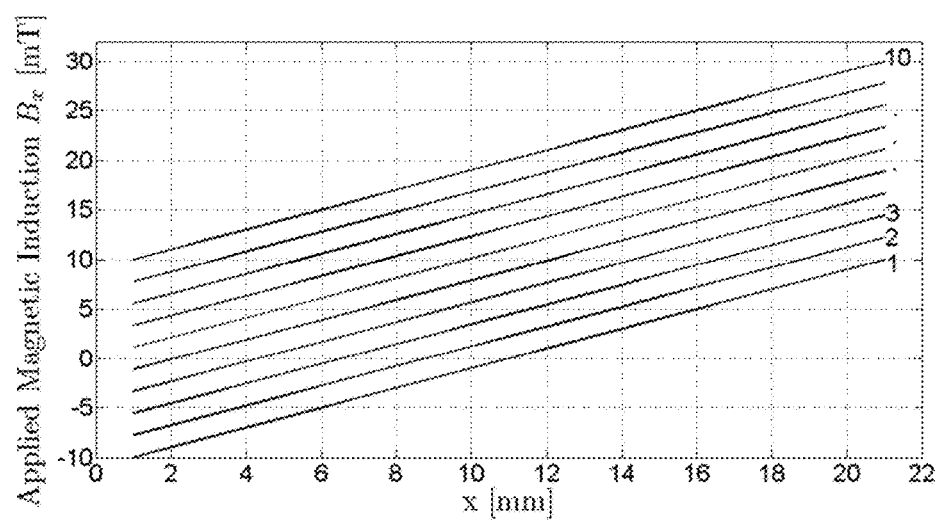
FIG. 7 illustrates examples of a set of different applied gradient fields in one direction, as used for simulations illustrating features according to embodiments of the present invention.
Figure 8:
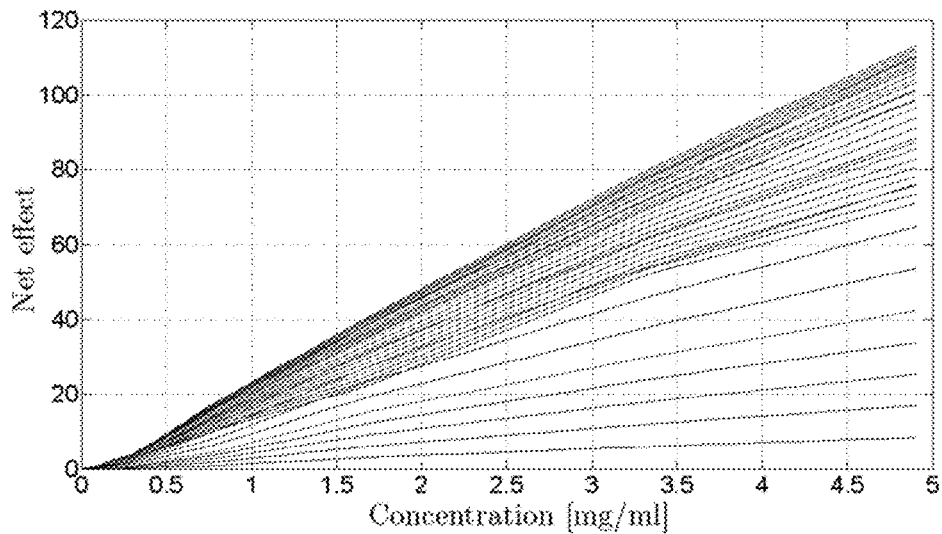
FIG. 8 illustrates a linear net effect is obtained using the calibration functions as shown in FIG. 6.
Figure 9:
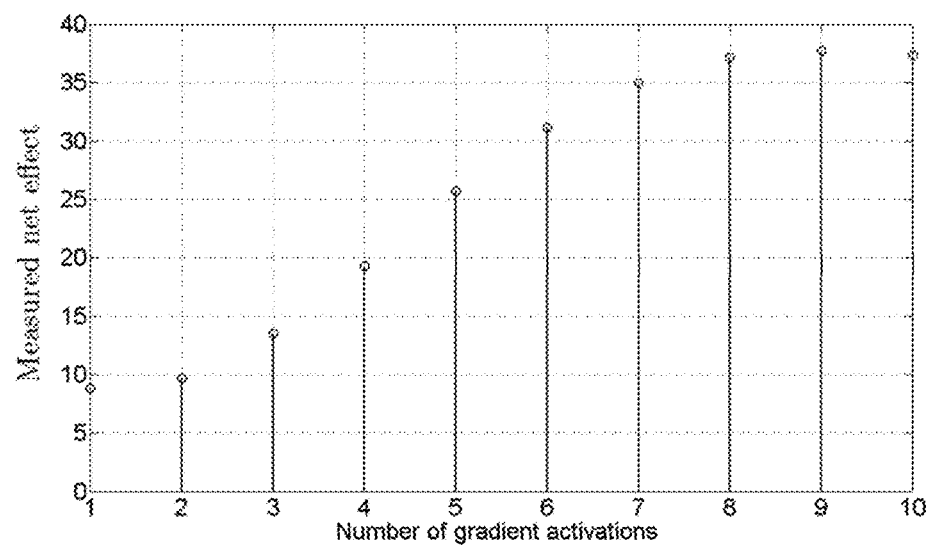
FIG. 9 illustrates the net effect measurements for certain concentrations using the conditions described in FIG. 5 to FIG. 8.

For the quantitative imaging, the following set of spatially varying magnetic fields is applied. FIG. 7 illustrates an example of 10 spatially varying applied magnetic inductions that are sequentially applied by using a gradient magnetic field of −10 mT to 10 mT over the region of 20 mm, yielding gradient of 1 T/m, and where a Helmholtz homogeneous field is applied with steps of 2.2 mT. These 10 sequential gradient fields are necessary so to obtain different measurements for the reconstruction of the magnetic nanoparticles.

Figure 6:
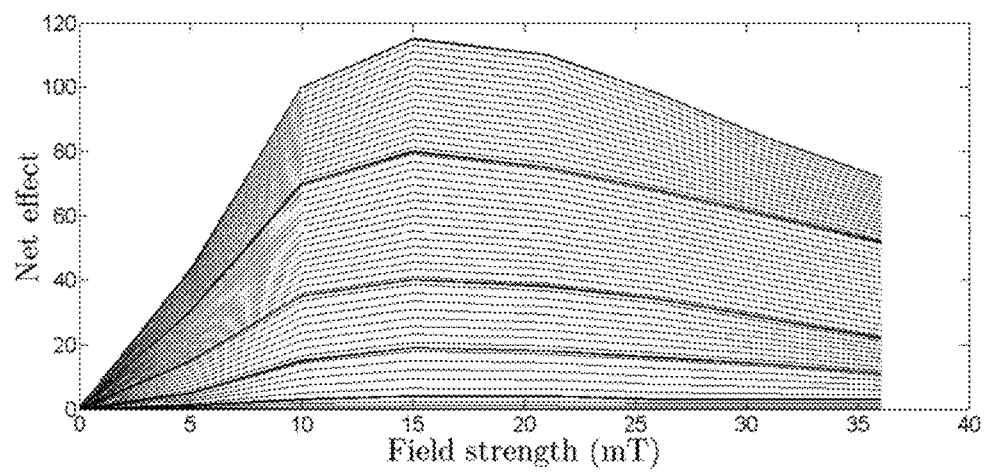
FIG. 6 illustrates calibration functions for different concentration values and Field strengths as used in simulations illustrating features according to embodiments of the present invention.

Using a method according to an embodiment of the present invention, the inverse solver used, uses the following assumption: the calibration function is linear with respect to the concentration: $f(B,C)=g(B)*C$. This is approximately the case here with respect to the given calibration function. It thus is allowed in the present example to have a nonlinear relationship of the calibration function with respect to B. It is to be noticed that it is possible to deal with nonlinearities in the calibration function. When applying the 10 gradient activations of FIG. 7 for the test concentration in FIG. 5 (above) and with calibration function of FIG. 6, we obtain the following net effect measurements.

Figure 10:
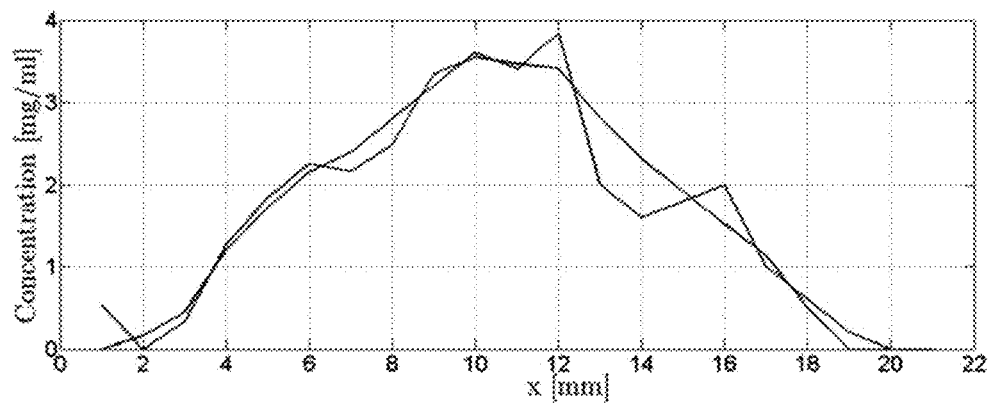
FIG. 10 illustrates a reconstructed concentration profile, illustrating features of method embodiments according to the present invention.

Starting from these numerical 'measurements', the distribution of the concentration reconstructed using the inverse solver is shown in FIG. 10. These results were obtained without incorporating the accurate magnetic induction variation (variation on the idealized magnetic induction shown in FIG. 7) so to have a more accurate forward solver. This will increase the accuracy of the inverse problem. So, theoretically, with assumptions and simple representations of magnetic fields, the present example illustrates that the methods are able to spatially reconstruct the distribution of magnetic nanoparticle concentrations in EPR.

Figure 11:
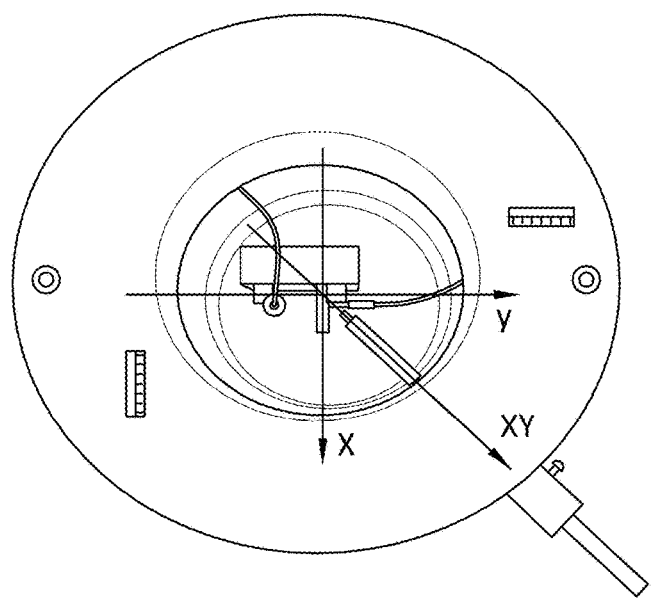
FIG. 11 illustrates an experimental setup whereby for the example shown movement of the sample was performed along the positive XY-axis, as used in the example illustrating features of embodiments of the present invention.

In a second example, results are illustrated using EPR measurements. First the response function and forward model is described. A one dimensional reconstruction through screening was performed, i.e. the sample is moved in the vicinity of the excitation and measurement coils. The response function vs position was measured. Measurements of Resovist 18.8 (18.8 µmol), Resovist J (0.29 µmol), Resovist K (0.15 µmol) and Resovist L (0.07 µmol) (shielded, results of 11 averaged measurements) were used to obtain the response function. The measurements were performed for the positive XY-axis with a discretization of 1 mm, as shown in FIG. 11.

Figure 12:
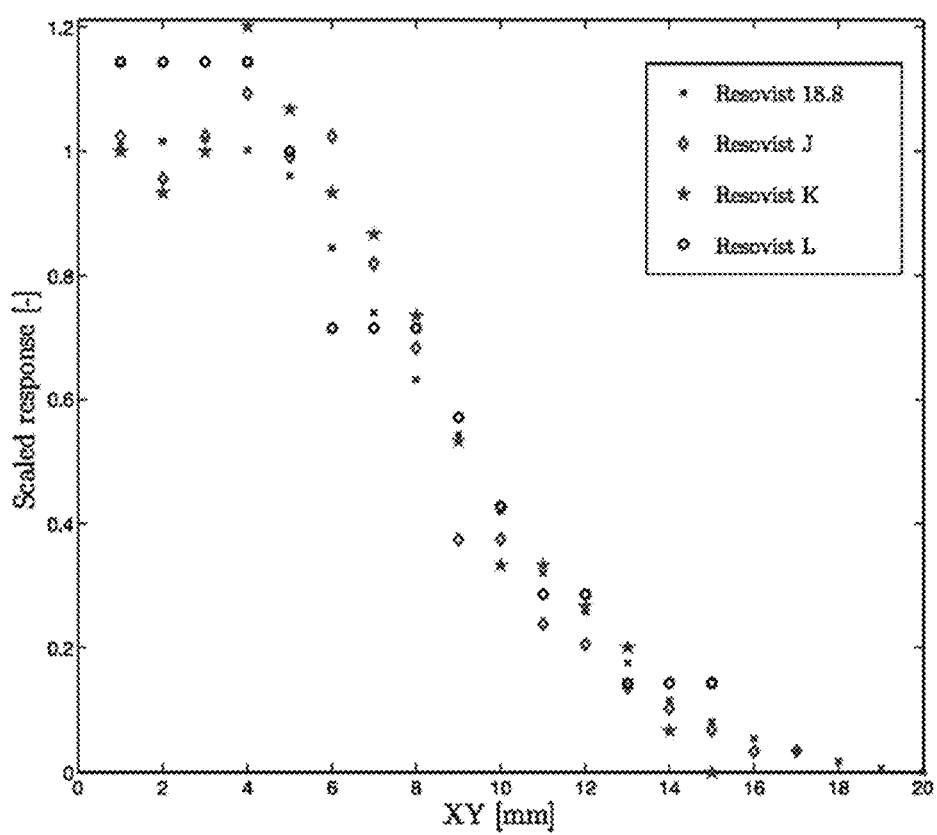
FIG. 12 illustrates measured response functions for the situation shown in FIG. 11.
Figure 13:
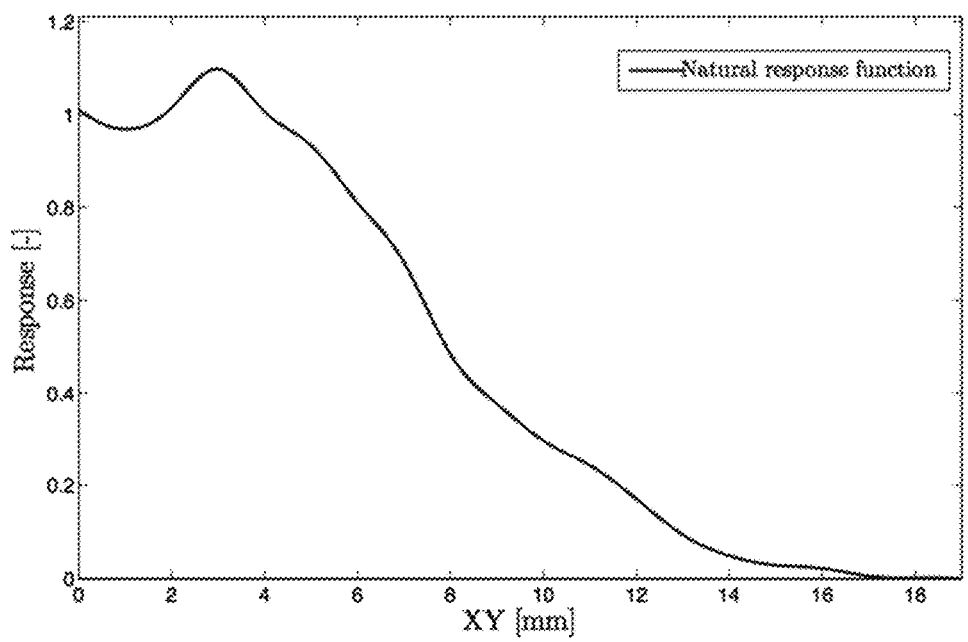
FIG. 13 illustrates the natural response function, as used in an example illustrating features of embodiments of the present invention.
Figure 14A:
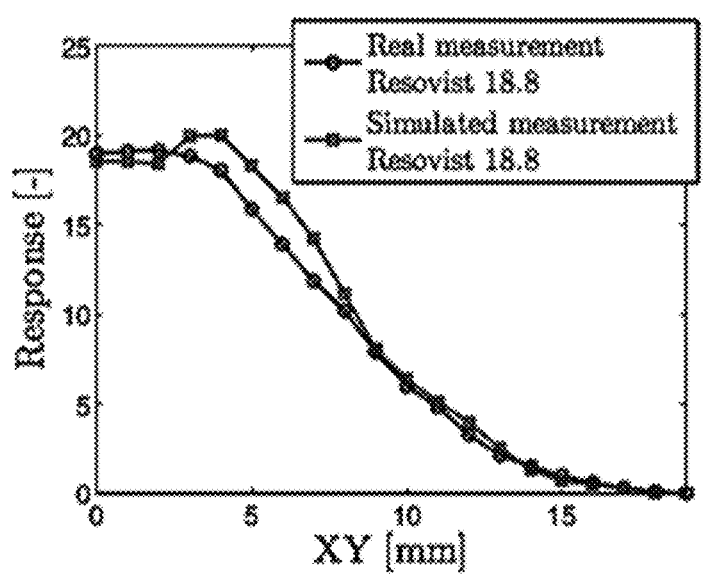
FIG. 14A to FIG. 14D illustrates a comparison of the performed measurements and the simulated measurements, illustrating features of embodiments of the present invention.
Figure 14B:
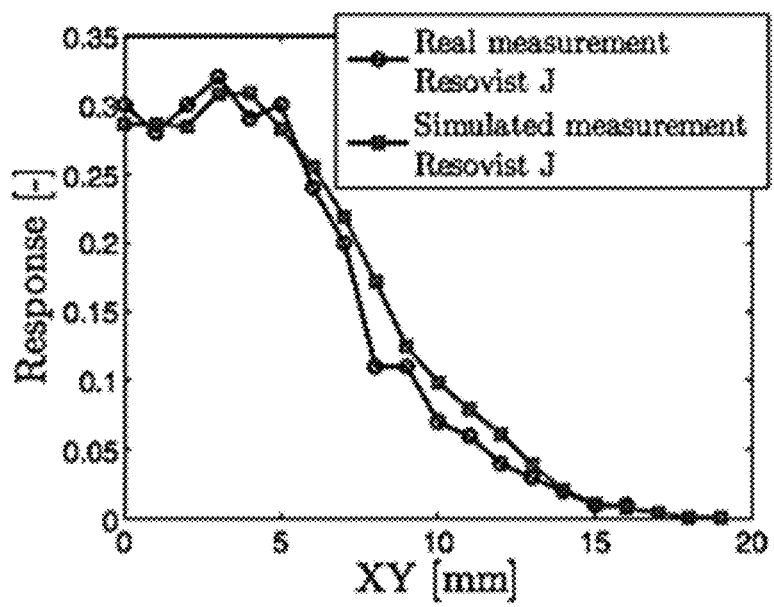
Figure 14C:
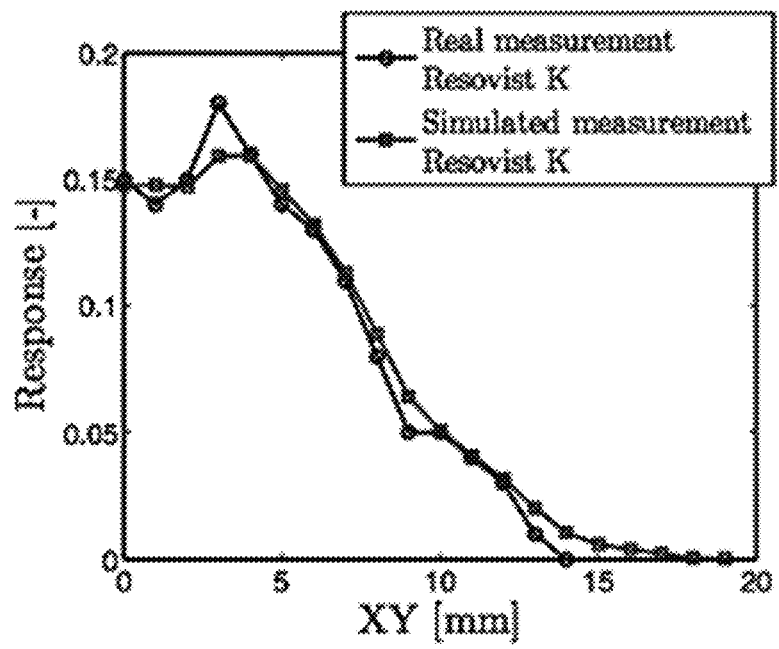
Figure 14D:
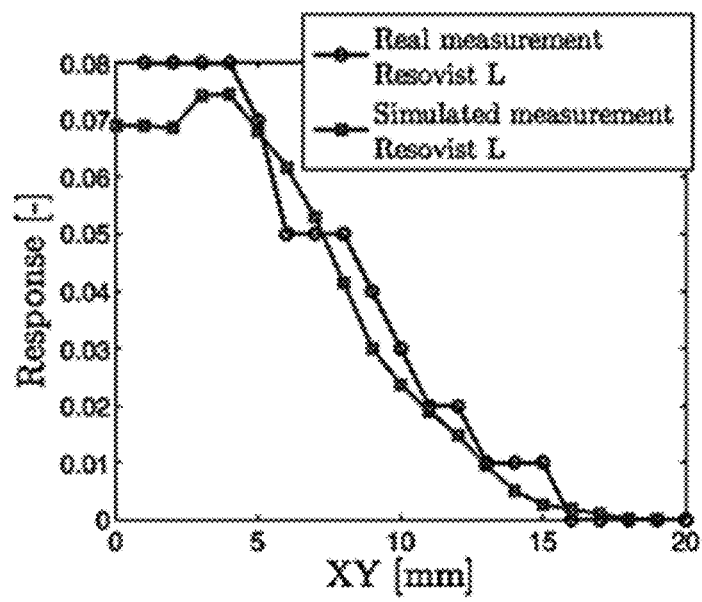

The response function was measured (i.e. measurements at different points in EPR) for the 4 different samples described above. The measured response functions are shown in FIG. 12. Using the response function from the previous example, a forward model was developed. First the response function was extended to a 'natural response function', with a discretization $\Delta N$ of 0.1 mm, using splines, as shown in FIG. 13.

The forward model used in the present example is based on the above response functions. As an example, FIG. 14A to FIG. 14D shows measurements that are sensitive to the distribution of particles. We observe correspondence between the forward model and the real measurements of the different particles. The discrepancy between forward and real measurements is here mainly because of noise and changes in the system (for example temperature).

Figure 15:
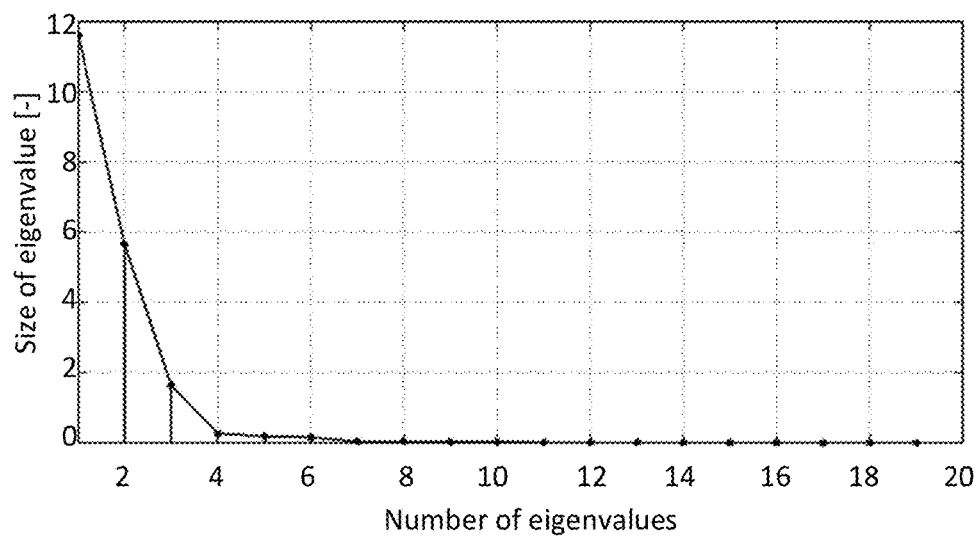
FIG. 15 illustrates the eigenvalue distribution for a measurement resolution of 1 mm and a reconstruction resolution of 1 mm, as used in an example illustrating features of embodiments of the present invention.

In a following step of the description of the experiment, the screening is discussed. Using measurements it is possible to reconstruct the spatial variation of the magnetic nanoparticles. Inversion of the system matrix is performed. The results shown here are for a reconstruction resolution of 1 mm. This means that if one has two magnetic nanoparticle sources, with a certain concentration and separated by a distance of 1 mm, these sources should be reconstructed with their respective concentrations. FIG. 15 shows the distribution of the eigenvalues for the Leadfield matrix L used. These eigenvalues represent the sensitivities of the response function for a measurement resolution of 1 mm and a reconstruction resolution of 1 mm. In total there are 19 eigenvalues. The eigenvalue distribution is dependent on the reconstruction and measurement resolution.

In the following section, the handling of eigenvalues will be discussed in some more detail, including an advantageous embodiment of the present invention whereby selection of the optimal eigenvalues is based on the processing according to an embodiment of the present invention. The selection of the optimal eigenvalue distribution can be obtained by proposing an internal optimization loop that determines numerically the best eigenvalues that give the best reconstruction quality. To investigate the influence of a measurement error on the reconstruction, the correlation coefficient for different concentrations using different noise levels were compared. The obtained construction result is dependent on the number of used eigenvalues. For lower noise levels, one should use more eigenvalues. The latter can be explained by the fact that in this case most eigenvalues represent signal sources instead of noise sources.

Figure 16:
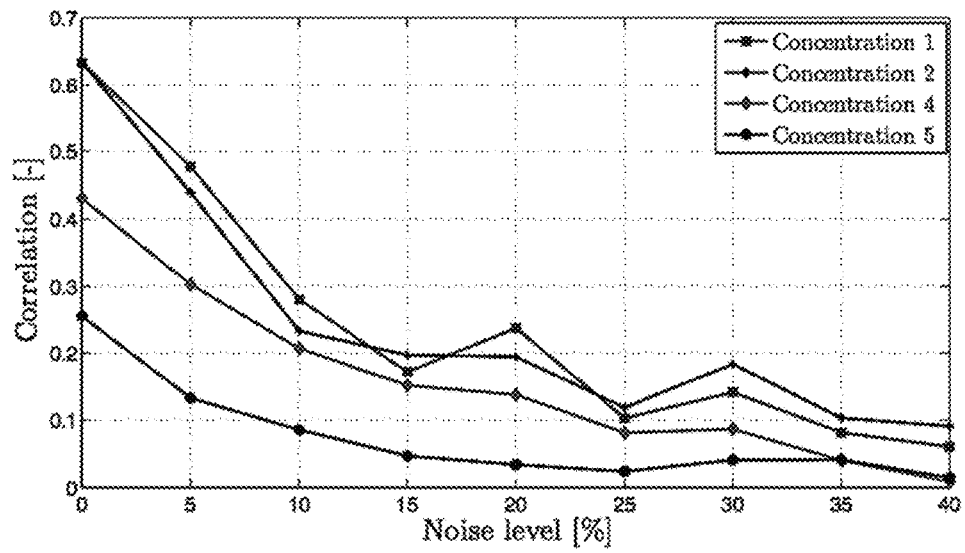
FIG. 16 illustrates the influence of noise on the reconstruction quality for the case of 5 retained eigenvalues, illustrating features of embodiments of the present invention.

In FIG. 16, a big decrease in reconstruction quality can be seen when increasing the noise to 10%. When more eigenvalues are retained the decrease is even steeper. After the noise level of 10% a more gradual decrease of the reconstruction quality is noticed. The noise level should be as low as possible, preferably below 5-10%. The reconstruction scores are the result of 50 averaged simulations.

Figure 17:
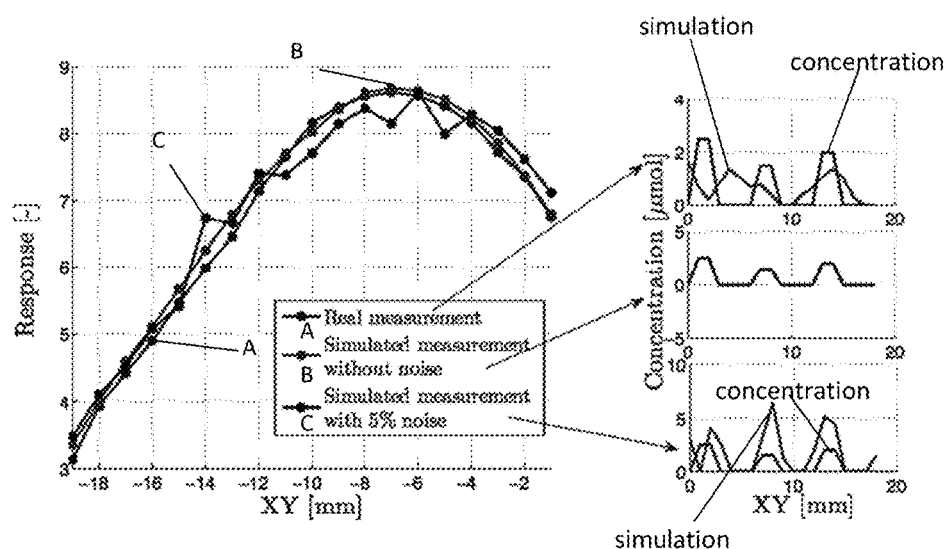
FIG. 17 illustrates responses of a real measurement, simulated measurement without noise and a simulated measurement with noise, illustrating features of embodiments of the present invention.

The differences between the results of the forward model and the real measurements were also compared, allowing to investigate what the error will be in the reconstruction, when a certain difference is present between the measured and simulated measurements. FIG. 17 shows an example of a measurement, a simulated measurement without noise and a simulated measurement with noise and the corresponding reconstructions. The differences between the responses cause errors on the reconstructions.

Figure 18:
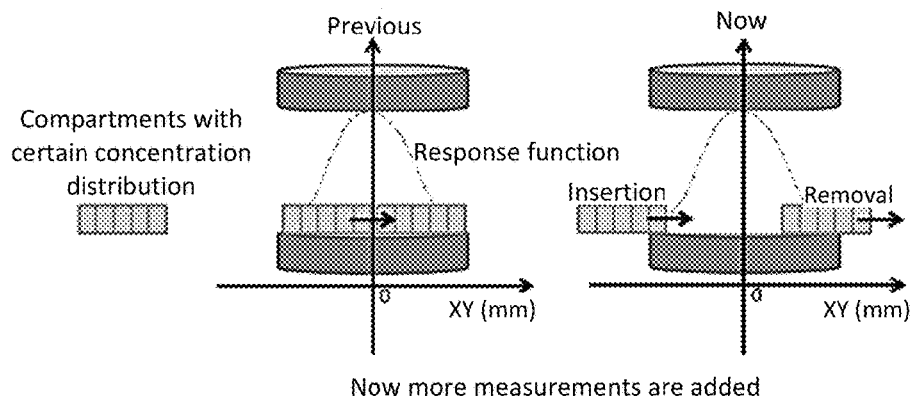
FIG. 18 illustrates the inclusion of measurements that also consider the insertion and removal of the concentration with respect to the magnetic field, illustrating features of embodiments of the present invention.
Figure 19:
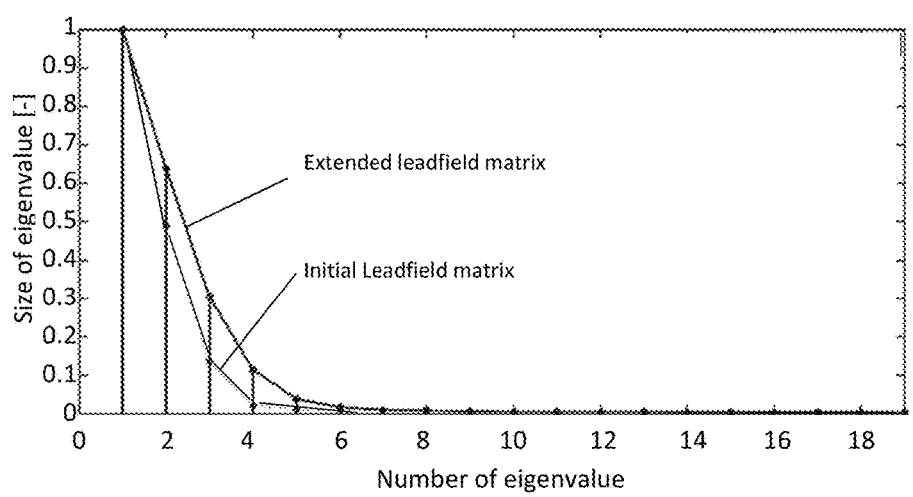
FIG. 19 illustrates the effect of the inclusion of measurements according to FIG. 14 on the eigenvalue distribution.

Further, also the impact of the leadfield matrix was discussed. A first used Leadfield matrix only considered the concentration distribution inside the magnetic field (meaning that for every element of the concentration distribution there exists a corresponding response function value). Initially a low condition number was obtained for the Leadfield matrix, however due to changes of the response function (more measurements) this condition number became higher. The condition number should be as low as possible, as a condition number shows the extent to which a calculated value (in our case the reconstruction) will change, when fixed parameters are changed (our Leadfield matrix). A high condition number means a big difference in reconstruction values for only a small change of the Leadfield values. This means that a response function with a small error, will have a major effect on the reconstruction. The Leadfield matrix was therefore extended with more measurements. These measurements also consider the insertion and removal of the concentration with respect to the magnetic field, as indicated in FIG. 18. This means rows are added that contain zeros (concentration elements that are on a position where there is no response anymore). Surprisingly, the zeros did not cause a higher noise sensitivity of the Leadfield matrix (i.e. the newly added measurements did not contain mostly noise and did add more information for the reconstruction step). Extending the Leadfield Matrix resulted in a different eigenvalue distribution. FIG. 19 shows the (normalized) eigenvalues.

Figure 20:
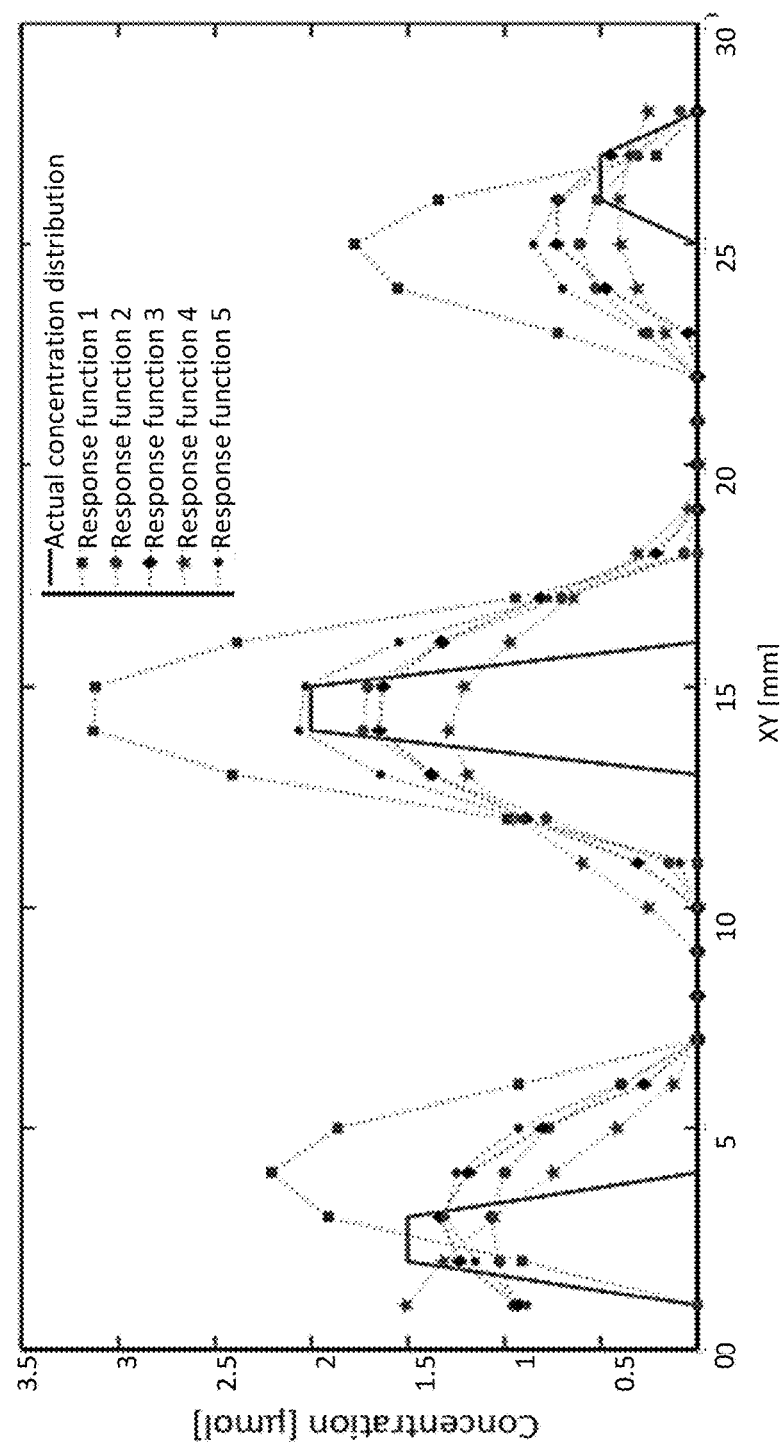
FIG. 20 illustrates the effect of the response function used on the reconstructed concentration profile, illustrating features of embodiments of the present invention.

Finally, also the reconstruction results are discussed in some more detail. The above experiment illustrates that, using the methods and systems according to embodiments of the present invention, one is able to reconstruct the actual concentration distribution. The accuracy depends on the used response function (that varies due to different temperature). An overview of the obtained results for different response functions is given in FIG. 20.

The invention claimed is:

1. A system for determining a reconstruction of a particle distribution in an object based on electron paramagnetic resonance measurement data of the object comprising the distribution of particles, the system comprising
a data input configured for receiving electron paramagnetic resonance measurement data of the object under study,
a processor programmed for processing the obtained electron paramagnetic resonance measurement data, the processor being programmed for applying a numerical model for solving a numerical inverse problem of deriving from the electron paramagnetic resonance measurement data a reconstruction of the particle distribution, the processor comprising a quality determinator programmed for determining a measure of the quality of the reconstructed particle distribution expressing the way the reconstruction coincides or approaches the electron paramagnetic resonance measurement data, and
the system comprising a controller for controlling the processing of the data by adjusting the numerical model as a function of the determined measure of the quality,
an output port configured for outputting data based on the derived reconstruction of the particle distribution.

2. A system according to claim 1, wherein the processor is programmed for deriving a reconstruction of the particle concentration profile.

3. A system according to claim 1, wherein the controller comprises a parameter selector configured for selecting a parameter of the numerical model.

4. A system according to claim 3, wherein controller is configured for altering a set of eigenvalues of the numerical problem solved using the numerical model, depending on the determined measure of quality of the reconstructed particle distribution.

5. A system according to claim 1, wherein the system comprises a feedback loop comprising the quality determinator and wherein the feedback loop is configured for controlling the system so as to obtain further electron paramagnetic resonance measurement data of the object.

6. A system according to claim 5, the data input comprising an EPR measurement system for measuring EPR measurement data, wherein the feedback loop is configured for controlling the EPR measurement system for obtaining further measurement data with an altered measurement condition for the object.

7. A system according to claim 5, wherein the feedback loop is configured for controlling the data input so as to obtain further EPR measurement data.

8. A system according to claim 7, wherein the feedback loop is configured for controlling the data input so as to obtain further EPR measurement data of the object sampled at different or additional relative positions of a magnetic field of the EPR system with respect to the object, sampled using different or additional gradient magnetic fields applied to the object, or sampled using a different spatial sampling point distribution over the sample.

9. A system for obtaining electron paramagnetic resonance data of an object, the system comprising a system for determining a reconstruction of a particle distribution in an object as described in claim 1.

10. A method for determining a reconstruction of a particle distribution in an object based on electron paramagnetic resonance measurement data of the object comprising the distribution of particles, the method comprising
obtaining electron paramagnetic resonance measurement data of the object under study,
processing the obtained data by applying a numerical model for solving a numerical inverse problem of deriving from the electron paramagnetic resonance measurement data a reconstruction of the particle distribution,
determining a measure of the quality of the reconstructed particle distribution expressing the way the reconstruction coincides or approaches the electron paramagnetic resonance measurement data, controlling the processing of the data by adjusting the numerical model as a function of the determined measure of the quality, and outputting data based on the derived reconstruction of the particle distribution.

11. A method according to claim 10, wherein said processing comprises deriving a reconstruction of the particle concentration profile.

12. A method according to claim 10, wherein said controlling comprises selecting a parameter of the numerical model or selecting comprises altering a set of eigenvalues of the numerical problem solved using the numerical model, depending on the determined measure of quality of the reconstructed particle distribution.

13. A method according to claim 10, wherein the method comprises obtaining further electron paramagnetic resonance measurement data of the object, based on the determined measure of quality of the reconstructed particle distribution and/or wherein the method comprises obtaining further measurement data for an altered measurement condition for the object.

14. A method according to claim 13, wherein the method comprises controlling the data input so as to obtain further EPR measurement data and/or wherein the method comprises obtaining further EPR measurement data of the object sampled at different or additional relative positions of a magnetic field of the EPR system with respect to the object, sampled using different or additional gradient magnetic fields applied to the object, or sampled using a different spatial sampling point distribution over the sample.

15. A computer program product for, if implemented on a processing unit, performing a method for determining a reconstruction of a particle distribution in an object based on electron paramagnetic resonance measurement data of the object comprising the distribution of particles, the method comprising obtaining electron paramagnetic resonance measurement data of the object under study, processing the obtained data by applying a numerical model for solving a numerical inverse problem of deriving from the electron paramagnetic resonance measurement data a reconstruction of the particle distribution, determining a measure of the quality of the reconstructed particle distribution expressing the way the reconstruction coincides or approaches the electron paramagnetic resonance measurement data, controlling the processing of the data by adjusting the numerical model as a function of the determined measure of the quality, and outputting data based on the derived reconstruction of the particle distribution.

16. A data carrier comprising a computer program product according to claim 15.

* * * * *